United States Patent
daCosta et al.

(10) Patent No.: US 8,548,824 B1
(45) Date of Patent: Oct. 1, 2013

(54) SYSTEMS AND METHODS FOR NOTIFYING OF DUPLICATE PRODUCT PRESCRIPTIONS

(75) Inventors: Patricia A. daCosta, Marietta, GA (US); Patrick I. Harris, Sr., Atlanta, GA (US)

(73) Assignee: McKesson Financial Holdings Limited (BM)

( * ) Notice: Subject to any disclaimer, the term of this patent is extended or adjusted under 35 U.S.C. 154(b) by 270 days.

(21) Appl. No.: 12/748,129

(22) Filed: Mar. 26, 2010

(51) Int. Cl.
*G06Q 50/00* (2012.01)

(52) U.S. Cl.
USPC .............................................. 705/3

(58) Field of Classification Search
USPC .............................................. 705/3
See application file for complete search history.

(56) References Cited

U.S. PATENT DOCUMENTS

| | | |
|---|---|---|
| 4,547,851 A | 10/1985 | Kurland |
| 5,048,870 A | 9/1991 | Mangini et al. |
| 5,235,702 A | 8/1993 | Miller |
| 5,301,105 A | 4/1994 | Cummings |
| 5,359,509 A | 10/1994 | Little et al. |
| 5,544,044 A | 8/1996 | Leatherman |
| 5,550,734 A | 8/1996 | Tarter et al. |
| 5,628,530 A | 5/1997 | Thornton |
| 5,644,778 A | 7/1997 | Burks et al. |
| 5,704,044 A | 12/1997 | Tarter et al. |
| 5,737,539 A | 4/1998 | Edelson et al. |
| 5,740,268 A | 4/1998 | Nishikawa et al. |
| 5,748,907 A | 5/1998 | Crane |
| 5,749,907 A | 5/1998 | Mann |
| 5,832,447 A | 11/1998 | Rieker et al. |
| 5,845,255 A | 12/1998 | Mayuad |
| 5,892,900 A | 4/1999 | Ginter et al. |
| 5,915,971 A | 6/1999 | Ramsay et al. |
| 5,950,169 A | 9/1999 | Borghesi et al. |
| 5,950,630 A | 9/1999 | Portwood et al. |
| 5,956,736 A | 9/1999 | Hanson et al. |
| 5,958,930 A | 9/1999 | Gangjee |
| 5,963,915 A | 10/1999 | Kirsch |
| 5,991,750 A | 11/1999 | Watson |

(Continued)

FOREIGN PATENT DOCUMENTS

| | | |
|---|---|---|
| CA | 2482370 A1 | 3/2006 |
| EP | 1310895 A2 | 11/2002 |

(Continued)

OTHER PUBLICATIONS

Notice of Allowance for U.S. Appl. No. 10/339,000 mailed Apr. 9, 2009.

(Continued)

*Primary Examiner* — Hiep V Nguyen
(74) *Attorney, Agent, or Firm* — Sutherland Asbill & Brennan LLP

(57) ABSTRACT

Embodiments of the invention may include systems and methods for notifying a prescriber or other entity of duplicate product prescriptions. According to one embodiment, a method for processing prescriptions is provided that may include the operations of: receiving a healthcare transaction that identifies a current prescribed product, a patient, and a current prescriber who prescribed the current prescribed product; retrieving patient history for the patient; determining the following based on the patient history: that the patient has previously received a previous equivalent product equivalent to the current prescribed product identified in the healthcare transaction and an identity of a previous prescriber of the previous equivalent product; and transmitting a notification to at least one of the previous prescriber or the current prescriber, wherein the notification identifies potential duplicate products.

18 Claims, 5 Drawing Sheets

(56) References Cited

U.S. PATENT DOCUMENTS

| | | |
|---|---|---|
| 6,006,242 A | 12/1999 | Poole et al. |
| 6,012,035 A | 1/2000 | Freeman et al. |
| 6,073,104 A | 6/2000 | Field |
| 6,195,612 B1 | 2/2001 | Pack-Harris |
| 6,202,923 B1 | 3/2001 | Boyer et al. |
| 6,224,387 B1 | 5/2001 | Jones |
| 6,272,472 B1 | 8/2001 | Danneels et al. |
| 6,307,940 B1 | 10/2001 | Yamamoto et al. |
| 6,324,516 B1 | 11/2001 | Shults et al. |
| 6,330,546 B1 | 12/2001 | Gopinathan et al. |
| 6,341,265 B1 | 1/2002 | Provost et al. |
| 6,343,271 B1 | 1/2002 | Peterson et al. |
| 6,427,020 B1 | 7/2002 | Rhoads |
| 6,529,892 B1 | 3/2003 | Lambert |
| 6,632,251 B1 | 10/2003 | Rutten et al. |
| 6,671,692 B1 | 12/2003 | Marpe et al. |
| 6,671,693 B1 | 12/2003 | Marpe et al. |
| 6,694,334 B2 | 2/2004 | DuLong et al. |
| 6,714,918 B2 | 3/2004 | Hillmer et al. |
| 6,757,898 B1 | 6/2004 | Ilsen et al. |
| 6,769,228 B1 | 8/2004 | Mahar |
| 6,879,959 B1 | 4/2005 | Chapman et al. |
| 6,978,286 B2 | 12/2005 | Francis et al. |
| 7,013,284 B2 | 3/2006 | Guyan et al. |
| 7,028,723 B1 | 4/2006 | Alouani et al. |
| 7,111,173 B1 | 9/2006 | Scheidt |
| 7,155,397 B2 | 12/2006 | Alexander et al. |
| 7,356,460 B1 | 4/2008 | Kennedy et al. |
| 7,380,707 B1 | 6/2008 | Fredman |
| 7,401,027 B2 | 7/2008 | Moore et al. |
| 7,418,400 B1 | 8/2008 | Lorenz |
| 7,490,047 B2 | 2/2009 | Brown et al. |
| 7,490,049 B2 | 2/2009 | Miller et al. |
| 7,493,263 B2 | 2/2009 | Helmus et al. |
| 7,519,540 B2 * | 4/2009 | Mayaud ............................ 705/2 |
| 7,555,435 B2 | 6/2009 | Ball et al. |
| 7,711,583 B2 | 5/2010 | Epstein et al. |
| 7,716,068 B2 | 5/2010 | Ball et al. |
| 7,720,694 B2 | 5/2010 | Potuluri et al. |
| 7,801,642 B2 | 9/2010 | Ansari et al. |
| 8,046,242 B1 | 10/2011 | daCosta et al. |
| 2001/0001014 A1 | 5/2001 | Akins, III et al. |
| 2001/0032099 A1 | 10/2001 | Joao |
| 2001/0037216 A1 | 11/2001 | Oscar et al. |
| 2001/0037224 A1 | 11/2001 | Eldridge et al. |
| 2001/0041993 A1 | 11/2001 | Campbell |
| 2001/0056358 A1 | 12/2001 | Dulong et al. |
| 2002/0002495 A1 | 1/2002 | Ullman |
| 2002/0035488 A1 | 3/2002 | Aquila et al. |
| 2002/0042725 A1 | 4/2002 | Mayaud |
| 2002/0044043 A1 | 4/2002 | Chaco et al. |
| 2002/0049617 A1 | 4/2002 | Lencki et al. |
| 2002/0055856 A1 | 5/2002 | Adams |
| 2002/0065687 A1 | 5/2002 | Onoue |
| 2002/0087554 A1 | 7/2002 | Seelinger |
| 2002/0087583 A1 | 7/2002 | Morgan et al. |
| 2002/0111832 A1 | 8/2002 | Judge |
| 2002/0120473 A1 | 8/2002 | Wiggins |
| 2002/0128883 A1 | 9/2002 | Harris |
| 2002/0133503 A1 | 9/2002 | Amar et al. |
| 2002/0138593 A1 | 9/2002 | Novak et al. |
| 2002/0175370 A1 | 11/2002 | Bockelman |
| 2002/0183979 A1 | 12/2002 | Wildman |
| 2002/0198831 A1 | 12/2002 | Patricelli et al. |
| 2003/0009357 A1 | 1/2003 | Pish |
| 2003/0009367 A1 | 1/2003 | Morrison |
| 2003/0028404 A1 | 2/2003 | Herron et al. |
| 2003/0050799 A1 | 3/2003 | Jay et al. |
| 2003/0074222 A1 | 4/2003 | Rosow et al. |
| 2003/0083903 A1 | 5/2003 | Myers |
| 2003/0120588 A1 | 6/2003 | Dodd et al. |
| 2003/0149594 A1 | 8/2003 | Beazley et al. |
| 2003/0149625 A1 | 8/2003 | Leonardi et al. |
| 2003/0154163 A1 | 8/2003 | Phillips et al. |
| 2003/0158755 A1 | 8/2003 | Neuman |
| 2003/0229540 A1 | 12/2003 | Algiene |
| 2004/0006490 A1 | 1/2004 | Gingrich et al. |
| 2004/0019464 A1 | 1/2004 | Martucci et al. |
| 2004/0039599 A1 | 2/2004 | Fralic |
| 2004/0046020 A1 | 3/2004 | Andreasson et al. |
| 2004/0054685 A1 | 3/2004 | Rahn et al. |
| 2004/0059600 A1 | 3/2004 | Ball |
| 2004/0059601 A1 | 3/2004 | Ball |
| 2004/0059602 A1 | 3/2004 | Ball |
| 2004/0059607 A1 | 3/2004 | Ball |
| 2004/0073457 A1 | 4/2004 | Kalies |
| 2004/0078234 A1 | 4/2004 | Tallal, Jr. et al. |
| 2004/0093242 A1 | 5/2004 | Cadigan et al. |
| 2004/0111291 A1 | 6/2004 | Dust et al. |
| 2004/0117323 A1 | 6/2004 | Mindala |
| 2004/0148198 A1 | 7/2004 | Kalies |
| 2004/0172281 A1 | 9/2004 | Stanners |
| 2004/0188998 A1 | 9/2004 | Henthorn |
| 2004/0249745 A1 | 12/2004 | Baaren |
| 2005/0015280 A1 | 1/2005 | Gabel et al. |
| 2005/0033604 A1 | 2/2005 | Hogan |
| 2005/0060201 A1 | 3/2005 | Connely, III et al. |
| 2005/0065821 A1 | 3/2005 | Kalies |
| 2005/0102169 A1 | 5/2005 | Wilson |
| 2005/0125292 A1 | 6/2005 | Kassab et al. |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240473 A1 | 10/2005 | Ayers, Jr. et al. |
| 2005/0288972 A1 | 12/2005 | Marvin et al. |
| 2006/0020514 A1 | 1/2006 | Yered |
| 2006/0026041 A1 | 2/2006 | Ullman |
| 2006/0039966 A1 | 2/2006 | Miller et al. |
| 2006/0085230 A1 | 4/2006 | Brill et al. |
| 2006/0136268 A1 | 6/2006 | Ash et al. |
| 2006/0149784 A1 | 7/2006 | Tholl et al. |
| 2006/0184391 A1 | 8/2006 | Barre et al. |
| 2006/0247948 A1 | 11/2006 | Ellis et al. |
| 2006/0259363 A1 | 11/2006 | Jhetam et al. |
| 2006/0271405 A1 | 11/2006 | Cipolle et al. |
| 2007/0005402 A1 | 1/2007 | Kennedy et al. |
| 2007/0050209 A1 | 3/2007 | Yered |
| 2007/0100662 A1 | 5/2007 | Suwalski et al. |
| 2007/0136100 A1 | 6/2007 | Daugherty et al. |
| 2007/0214009 A1 | 9/2007 | Epstein et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2008/0262868 A1 | 10/2008 | Malolepszy |
| 2008/0312957 A1 | 12/2008 | Luciano et al. |
| 2009/0210252 A1 * | 8/2009 | Silver ............................... 705/3 |
| 2009/0277516 A1 | 11/2009 | Winkler et al. |
| 2010/0010909 A1 | 1/2010 | Marshall et al. |
| 2011/0029321 A1 | 2/2011 | Rourke et al. |

FOREIGN PATENT DOCUMENTS

| | | |
|---|---|---|
| WO | WO 9106917 A1 | 5/1991 |
| WO | WO 9503569 A3 | 2/1995 |
| WO | WO 9725682 A1 | 7/1997 |
| WO | WO 9850871 A1 | 11/1998 |
| WO | WO 0039737 A1 | 7/2000 |
| WO | WO 2007025295 A2 | 3/2007 |

OTHER PUBLICATIONS

Final Office Action for U.S. Appl. No. 12/131,495 mailed Oct. 13, 2011.

Paul Brians, Common Errors in English Usage, Retrieved Nov. 21, 2007.

Non-Final Office Action for U.S. Appl. No. 12/121,495 mailed Apr. 12, 2011.

Final Office Action for U.S. Appl. No. 12/357,882 mailed Apr. 13, 2011.

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

"Two automatic identification technology, neither new in the sense if being recent developments . . ." Patient Safety & Quality Healthcare [Online] Aug. 2005. URL: http://www.awarix.com.

"Subnotebooks, Phones, and More. St. Vincent's Gets on Track." Mobile Health Data [Online], Nov. 19, 2004. URL: http://www.awarix.com.

"Coping with Information Overload." The News Source for Healthcare Information Technology [Online] Nov. 2004. URL: http://www.awarix.com.

"St. Vincent's first to use Birmingham startup's information system." The Birmingham News [Online] Apr. 11, 2005. URL: http://www.awarix.com.

"St. Vincent's is Digital Flagship" D. Lockridge; Birmingham Medical News [Online] Sep. 2005.

Untitled Webpage, "Apparatus, Method and Product for Multi-attribute Drug Comparison to Avoid Medical Errors" University of Illinois at Chicago, pp. 1-2, available at www.uic.edu.

1998 Conference Archive, "Enhancing Patient Safety and Reducing Errors to Health Care", pp. 1-9, available at www.npsf.org.

Webpage entitled: Institute for Safe Medication Practices, "Prescription mapping can improve efficiency while minimizing errors with look-alike products", available at www.ismp.org.

Webpage entitled: ISMP Quarterly Action Agenda: Oct.-Dec. 2001, Jan. 23, 2002; pp. 1-3, available at www.ismp.org.

PR Newswire, "NDCHealth Annouces NDC Rx Safety Advisor to Help Prevent Look-Alike Sound-Alike Dispensation Errors", New York: Aug. 12, 2002.p. 1.

FDA Alert, Aug. 8, 2008 Drugs, Information for Healthcare Professionals—Simvastatin (marketed as Zocor and generics), Ezetimibe/Simvastatin (marketed as Vytorin), Niacin extended-release/Simvastatin (marketed as Simcor), used with Amiodarone (Cordarone, Pacerone), obtained from fda.gov/Drugs/DrugSafety Website on Sep. 15, 2009.

Drug Sheet entitled: Generic Name: lovastatin, Brand Name: Mevacor, Altoprev.

Anonymous, Recommendations for the Use of 3-Hydroxy-3-methylglutaryl Coenzyme A Reductase Inhibitors (statins) i Veteran Patients Receiving Medications with the Potential for Drug-Drug Interactions, Nov. 2001.

Jerilyn B. Petropoulos and Christina E. Bello-Quintero, Frequency of Simvastatin Prescriptions with Potentially Interacting Mediations in a Veterans Affairs Health Care System, Journal of Managed Care Pharmacy, pp. 239-242, vol. 10, No. 3, May/Jun. 2004.

Joseph M. Kahwaji and Ryszard R. Dudek, How Can We Manage Hyperlipidemia and Avoid Rhabdomyolysis in Transplant Patients?, The Permanente Journal/Fall 2006/vol. 10, No. 3.

Huang, et al., Drug-Drug, Drug-Dietary Supplement, and Other Interactions, Regulatory Science. 2004.

Helen Fields, Doctors Often Ignore 'Black Box' Warnings on Prescription Drugs, Nov. 18, 2005.

How Often do Doctors Ignore Drug Interaction Warnings Generated by Electronic Prescribing Systems? Feb. 23, 2009, KevinMD.com—medical weblog.

Martin Kohl, Although There Aren't Any Perfect Solutions to Creating a Formulary Free of Drug-drug Interactions, There are Things You Can Do to Limit Problems, Managed Care, Sep. 1998.

Office Action dated Apr. 19, 2007, in U.S. Appl. No. 10/339,230.

Final Office Action dated Oct. 18, 2007 in U.S. Appl. No. 10/339,230.

Office Action dated Feb. 28, 2008 in U.S. Appl. No. 10/339,230.

Final Office Action dated Sep. 29, 2008 in U.S. Appl. No. 10/339,230.

Non-Final Office Action dated Mar. 27, 2009 in U.S. Appl. No. 10/339,230.

Notice of Allowance for U.S. Appl. No. 10/339,230, date mailed by USPTO, Apr. 9, 2009.

Final Office Action dated Sep. 11, 2009 in U.S. Appl. No. 10/339,230.

Office Action dated Aug. 22, 2007 in U.S. Appl. No. 10/339,000.

Office Action dated Mar. 17, 2008 in U.S. Appl. No. 10/339,000.

Final Office Action mailed Oct. 9, 2008 for U.S. Appl. No. 10/339,000.

Office Action dated Apr. 2, 2007 in U.S. Appl. No. 10/339,612.

Final Office Action dated Sep. 20, 2007 in U.S. Appl. No. 10/339,612.

Office Action dated Jan. 25, 2008 in U.S. Appl. No. 10/339,612.

Final Office Action dated Aug. 6, 2008 in U.S. Appl. No. 10/339,612.

Notice of Abandonment for Failure to Respond to Office Action for U.S. Appl. No. 10/339,612 mailed Mar. 31, 2009.

Office Action dated Jun. 21, 2005, in U.S. Appl. No. 10/339,108.

Office Action Dated Sep. 16, 2005, U.S. Appl. No. 10/339,108.

Final Office Action dated Mar. 16, 2006 in U.S. Appl. No. 10/339,108.

Final Office Action dated Sep. 7, 2006 in U.S. Appl. No. 10/339,108.

Office Action Dated Mar. 5, 2007, U.S. Appl. No. 10/339,108.

Final Office Action dated Aug. 23, 2007 in U.S. Appl. No. 10/339,108.

Notice of Abandonment for Failure to Respond to Office Action for U.S. Appl. No. 10/339,108 mailed Nov. 4, 2008.

Notice of Allowance for U.S. Appl. No. 12/357,882 mailed Aug. 5, 2011.

Non-Final Office Action for U.S. Appl. No. 12/571,152 mailed Dec. 5, 2011.

Final Office Action for U.S. Appl. No. 12/571,152 mailed Mar. 20, 2012.

Dundee, et al., "Pediatric Counseling and Medication Management Services: Opportunities for Community Pharmacies," Journal of the American Pharmaceutical Association. Jul./Aug. 2002, vol. 42, No. 4.

Walgreens, "Pharmacy Manual," Jan. 2010.

Allen, Loyd; "A Spoonful from Paddock Helps the Medicine Go Down," Secundum Artern, vol. 4, No. 2; 2007.

Shrewsbury, Bob; "Theophylline—Guaifenesin Syrup." University of North Carolina, Chapel Hill. Jan. 2011.

RS Software, "CompoundAssist Manual" 2002.

FDA, "Pediatric Dispensing Considerations," 2006.

Braun, "Pinnacle TPN Management System," Dec. 2006.

Herbein, Orsolya, "FLAVORx Favorable Flavors Program," 2009.

Cram et al., "Challenges of developing palatable oral paediatric formulations," International Journal of Pharmaceutics 365; 2009.

Non-Final Office Action for U.S. Appl. No. 12/121,495 mailed Mar. 13, 2013.

Non-Final Office Action for U.S. Appl. No. 13/040,710 mailed Apr. 3, 2013.

Compounding Today, "Ciprofloxacin Suspension in Syrup NF," 2009.

Non-Final Office Action dated Dec. 15, 2010 in U.S. Appl. No. 12/357,882.

* cited by examiner

SYSTEMS AND METHODS FOR NOTIFYING OF DUPLICATE PRODUCT PRESCRIPTIONS

FIELD OF THE INVENTION

Aspects of the invention relate generally to healthcare transactions, and more particularly, to systems and methods for notifying of duplicate product prescriptions.

BACKGROUND OF THE INVENTION

Any number of reasons exist that may result in a duplicate prescription to be written for a patient for the same or similar product. Some patients are high utilizers of medical services who may see multiple specialists for various conditions. Thus, one physician may prescribe a product to treat one condition, while a second physician prescribes the same or similar product (e.g., being a chemical equivalent, having equivalent therapeutic effects, etc.) to treat the same (or even a different) condition. Patients may not be aware that the products prescribed are the same. Different physicians may not have access to a patient's complete prescription history, and thus not be aware that a patient was previously prescribed the same or similar product. This may be the case especially when the two physicians are not part of the same practice group or operating entity, and thus do not have access to a patient's records maintained by the other physician. Other instances may lead to duplicate prescriptions of the same or similar products when patients attempt to over-utilize prescription products, such as controlled substances, by intentionally visiting different multiple prescribers for the purpose of obtaining multiple prescriptions for the desired drug. Accordingly, without complete access to a patient's prescription history, prescribers or pharmacists, the two most important medical professionals involved in patient care and drug utilization, are under-informed.

Thus, there is a need in the industry for systems and methods for notifying a prescriber or other entity of duplicate product prescriptions.

SUMMARY OF THE INVENTION

Some or all of the above needs and/or problems may be addressed by certain embodiments of the invention. Embodiments of the invention may include systems and methods for notifying a prescriber or other entity of duplicate product prescriptions. According to one embodiment, a method for processing prescriptions is provided. The method may include the operations of: receiving a healthcare transaction that identifies a current prescribed product, a patient, and a current prescriber who prescribed the current prescribed product, and retrieving patient history for the patient. The method may further include determining the following based on the patient history: that the patient has previously received an equivalent product that is equivalent to the current prescribed product identified in the healthcare transaction and an identity of a previous prescriber of the previous equivalent product. The method may also include transmitting a notification to at least one of the previous prescriber or the current prescriber, wherein the notification identifies potential duplicate products.

According to another embodiment of the invention, a system is provided. The system may include at least one memory for storing computer-executable instructions and at least one processor configured to access the memory. The processor may further be configured to execute the computer-executable instructions to: receive a healthcare transaction that identifies a current prescribed product, a patient, and a current prescriber who prescribed the current prescribed product; retrieve patient history for the patient; determine, based on the patient history: that the patient has previously received an equivalent product that is equivalent to the current prescribed product identified in the healthcare transaction and an identity of a previous prescriber for the previous equivalent product; and transmit a notification to at least one of the previous prescriber or the current prescriber, wherein the notification notifies of potential duplicate products.

BRIEF DESCRIPTION OF THE DRAWINGS

Reference will now be made to the accompanying drawings, which are not necessarily drawn to scale, and wherein.

DETAILED DESCRIPTION

Figure 1:
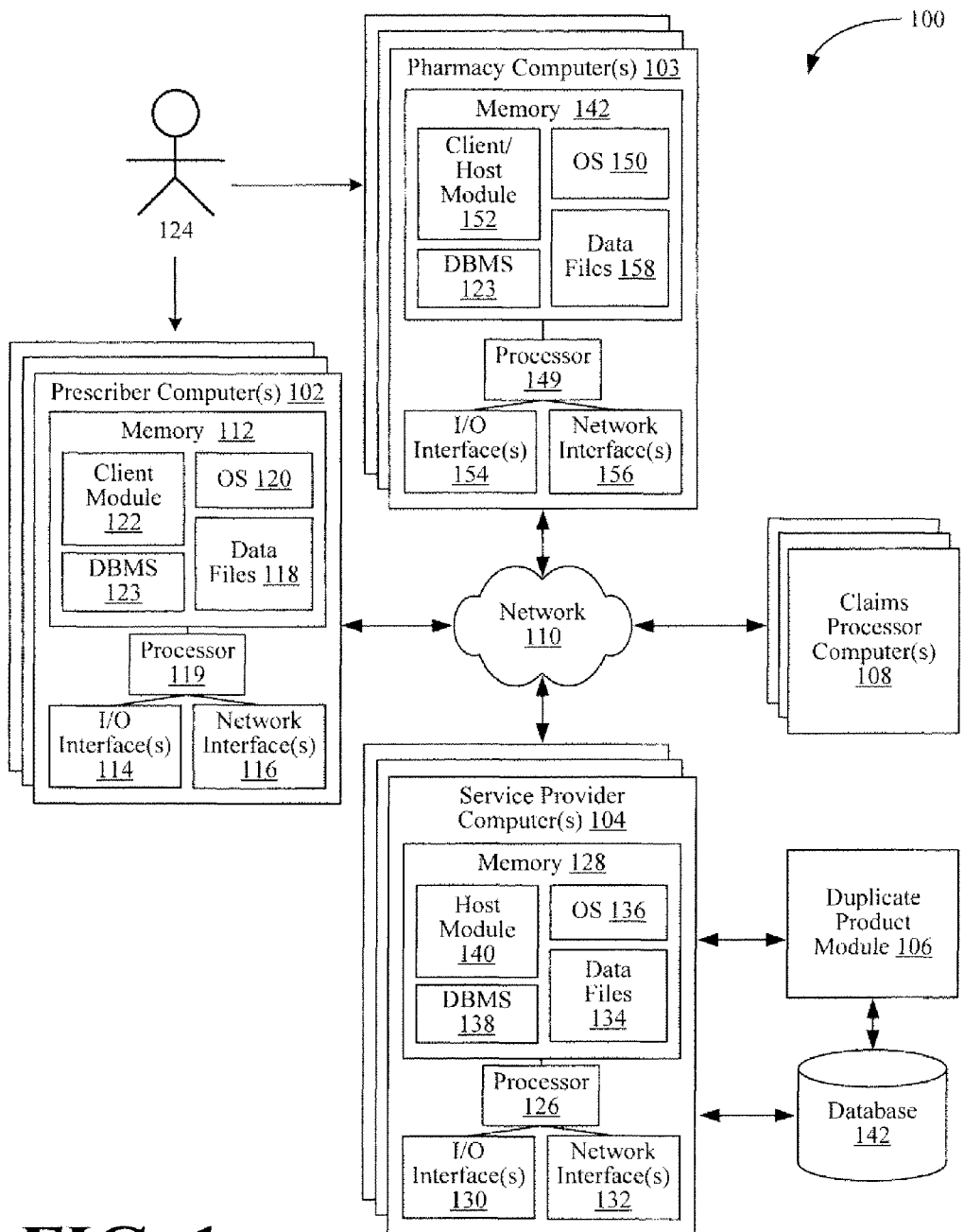
FIG. 1 illustrates an example system for notifying of duplicate product prescriptions, according to an example embodiment of the invention.

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Due to the possibility of a patient obtaining prescriptions for duplicate products from different physicians and/or filling these prescriptions at any number of different pharmacies, the medical professionals (e.g., prescribers and pharmacists) may not have complete visibility of a patient's entire patient history. Thus, prescribers and/or pharmacists may not be aware that they are prescribing or dispensing duplicate products, or that a patient may be intentionally or unintentionally obtaining and filling multiple prescriptions for the same product. However, a service provider that facilitates handling and processing healthcare transactions related to patient prescriptions (e.g., a routing switch) can provide significant value as a result of the interaction between multiple pharmacies, prescribers, and claim processors. By facilitating the processing and transmission of healthcare transactions, a service provider has access to and can store valuable data related to a patient's prescription history. Therefore, as described in more detail herein, a service provider that captures and maintains patient history, in part due to its unique relationship and access to multitudes of patient transactions, may perform further analysis of a healthcare transaction related to a patient's prescription to determine whether the currently prescribed product is the same as or similar to one already prescribed for and dispensed to the patient. Moreover, because it processes transactions from multiple prescribers and multiple pharmacies that are unaffiliated, the service provider is also uniquely positioned to generate and maintain a more complete view of a patient's history, capturing information from unrelated entities that would otherwise not be combined. Thus, the service provider therefore can make these determinations and perform subsequent notifications to the various persons or entities associated therewith.

For example, according to one embodiment, a service provider, upon receiving a healthcare transaction that identifies a current prescribed product (e.g., a prescription claim request from a pharmacy or an electronic prescription order from a prescriber), can analyze the patient's medical history. To determine whether there may exist a potentially duplicate prescription, the service provider can compare the current prescribed product against previously prescribed products for the patient. If one or more equivalent products are identified, various other factors may optionally be analyzed to determine whether notification is warranted, such as, but not limited to, whether the two products were prescribed by different physicians (or unaffiliated physicians), or whether the prescriptions occurred within a predetermined period of time from each other (i.e., to indicate overlapping administration periods). Upon determining that notification is required, any number of parties and/or entities can be notified by the service provider, such as via email, facsimile, short message service (SMS) text message, telephone communication, mailed communications, network-based or Internet-based communications, and the like. For example, the first prescriber (e.g., physician) of the previous product may be notified that the patient has subsequently received and filled a potentially duplicate prescription for the same or similar product. Similarly, the new prescriber of the current prescription being analyzed may be notified, so the second prescriber may act accordingly, such as to contact the patient and suggest alternative therapy, or to update patient records to be aware of potentially fraudulent or suspect activities. Pharmacies, patients, and/or other entities may also be notified to alert them of the potential duplication.

Accordingly, embodiments of the invention can provide for the determination, and notification of, a potential duplicate product being prescribed to a patient. These embodiments are described more fully below with reference to the accompanying figures, in which embodiments of the invention are shown.

As used herein, the term "healthcare transaction" may generally refer to any transaction processed by a service provider that identifies a prescribed product, such as a prescription claim transaction received from a pharmacy for adjudication with a claims processor or an electronic prescription order (or e-prescribing transaction) received from a prescriber for to be filled by a pharmacy. The term "current prescribed product" is intended to generally refer to a product referenced in the current healthcare transaction being processed at a service provider. The term "previous equivalent product" is intended to generally refer to any product that has been prescribed to the patient in the past and which may potentially be an equivalent or duplicate of the current prescribed product, as determined by these systems and methods.

System Overview

FIG. 1 illustrates an example system that allows for notifying one or more prescribers or other entities or persons of potential duplicate product prescriptions, according to an example embodiment of the invention. The system 100 may include at least one prescriber computer 102, at least one pharmacy computer 103, at least one service provider computer 104, and at least one claims processor computer 108, each configured for accessing and reading associated computer-readable media having data and/or computer-executable instructions stored thereon for implementing the various methods described herein. Each of the prescriber computer 102, the pharmacy computer 103, the service provider computer 104, and the claims processor computer 108 may be in direct communication with each other and/or in communication via a network 110, which as described below can include one or more private and public networks, including the Internet. By executing computer-executable instructions, each of these computer systems may form a special-purpose computer or a particular machine. As used herein, the term "computer-readable medium" may describe any form of computer memory or memory device.

Although various computers are illustrated in, and described with reference to, FIG. 1, it is appreciated that each of these computers is associated with a respective entity. For example, a prescriber computer 102 is associated with and/or operated by a prescriber (e.g., a physician's office, etc.), a pharmacy computer 103 is associated with and/or operated by a pharmacy (e.g., a pharmacy or practice management system, etc.), a service provider computer 104 is associated with and/or operated by a service provider, and a claims processor computer 108 is associated with a third-party claims processor (e.g., a third-party payor, etc.). Moreover, multiple entities of the same type may participate, each associated with and/or operating one or more computers. For example, multiple prescribers and pharmacies may participate in the below-described operations, each associated with and/or operating one or more respective computers. FIG. 2C below illustrates an example where multiple service provider computers participate in the operations described herein. Similarly, for each of the computers described herein, it is appreciated that various components and features of each of the computers may also be provided in multiples (e.g., multiple processors, memory elements, application modules, etc.), but may be referred to herein in the singular for simplicity.

The prescriber computer 102, the pharmacy computer 103, and the service provider computer 104 may each be one or more processor-driven devices, such as, but not limited to, a server computer, a personal computer, a laptop computer, a handheld computer, and the like. In addition to having one or more processors 119, 149, 126, the prescriber computer 102, the pharmacy computer 103, and the service provider computer 104 may each further include one or more memories 112, 141, 128, one or more input/output (I/O) interfaces 114, 154, 130, and one or more network interfaces 116, 156, 132, respectively. The memories 112, 141, 128 may store data files 118, 158, 134 and various program modules, such as an operating system (OS) 120, 150, 136, a client and/or host module 122, 152, 140, and a database management system (DBMS) 123, 153, 138 for accessing one or more databases, respectively. The I/O interface(s) 114, 154, 130 may facilitate communication between the processors 119, 149, 126, respectively, and various I/O devices, such as a keyboard, mouse, printer, microphone, speaker, monitor, bar code reader/scanner, RFID reader, and the like. The network interfaces 116, 156, 132 each may take any of a number of forms, such as a network interface card, a modem, a wireless network card, and the like. Although not described or illustrated in detail, each claims processor computer 108 may be configured in the same or similar manner as described for each of the prescriber computer 102, the pharmacy computer 103, and the service provider computer 104.

With reference to the prescriber computer 102, the client module 122 may be an Internet browser or other software, such as a dedicated program, for interacting with the service provider computer 104 and/or one or more pharmacy computers 103. For example, a user, such as, but not limited to, a physician, a nurse, a technician, or an administrative assistant may utilize the client module 122 to initiate or direct an electronic prescription order to the service provider computer 104 for routing to a pharmacy computer 103. In addition, the prescriber computer 102 and its associated DBMS 123 may be operable to access one or more databases for storing and/or retrieving healthcare information, which may include, but is not limited to, patient history information.

With reference to the pharmacy computer 103, the client/host module 152 may be an Internet browser or other software, such as a dedicated program, for interacting with the service provider computer 104 and/or one or more prescriber computers 102. For example, a user, such as, but not limited to, a pharmacist, other pharmacy employee, physician, nurse, administrator, or a patient 124, may utilize the client/host module 152 to initiate or direct a healthcare transaction request, such as a prescription billing/claim request, to the service provider computer 104 for processing and/or routing to a claims processor computer 108 (e.g., a third-party payor computer, etc.) or to communicate with a prescriber computer 102. In addition, the pharmacy computer 103 and its associated DBMS 153 may be operable to access one or more databases for storing and/or retrieving healthcare information, which may include, but is not limited to, patient information, patient history, prescriber information, claims processor information, and the like.

The service provider computer 104 may be configured for receiving, processing, and fulfilling healthcare transaction requests from pharmacies, which may include, but are not limited to, performing claims adjudication processing, including performing pre- and/or post-adjudication editing; processing non-claim (e.g., 100% customer pay) payment transactions; and for processing electronic prescription orders between a prescriber and a pharmacy. In addition, as described herein, as part of processing healthcare transaction requests, the service provider computer 104 can be configured to determine whether a prescription indicated by a prescription claim request received from a pharmacy computer 103 or an electronic prescription order received from a prescriber computer 102 identifies a duplicate prescription for a same or similar product already dispensed to the patient previously. According to an example embodiment, the service provider computer 104 may comprise, but is not limited to, one or more specialized computers, such as "switches" or "switch providers" that perform routing and processing of healthcare transactions between healthcare providers (e.g., pharmacies, prescribers, hospitals, etc.), payors/claims processors, third parties, and/or other service providers.

The service provider computer 104 and its associated DBMS 138 may be operable to access one or more databases or data storage devices, such as a database 142, for storing and/or retrieving healthcare transaction information, claim routing information, claim adjustment criteria, prescribing information, and/or electronic prescription routing information, for example. According to one embodiment, the data files 134 of the service provider computer 104 may also store routing tables for determining the subsequent transmission of a prescription claim request or an electronic prescription order. For example, these routing tables may determine that particular prescription claim requests received from pharmacy computers 103 are associated with certain payors (e.g., pharmaceutical benefit managers (PBMs), insurance companies, etc.), and therefore specify a particular claims processor computer 108 where the prescription claim requests are routed. Similarly, routing tables may determine that particular electronic prescription orders received from prescriber computers 102 are intended for certain pharmacy computers 103 where the electronic prescription orders are to be routed. The host module 140 of the service provider computer 104 may initiate, receive, process, and respond to electronic prescription orders from the respective client module 122 of the prescriber computer 102, and, in response, may further initiate, receive, process, and respond to electronic prescription replies from the client/host module 152 of the pharmacy computer 103. Similarly, the host module 140 of the service provider computer 104 may initiate, receive, process, and respond to prescription claim requests from the respective client/host module 152 of a pharmacy computer 103, and, in response, may further initiate, receive, process, and respond to adjudicated prescription claim replies from a claims process or computer 108. The host module 140 may further be operative to direct the storage of information associated with various prescription and/or claim transactions in the data storage device or database 142, or otherwise retrieve information from stored data.

The service provider computer 104 may communicate with, or otherwise include, a duplicate product module 106. As described herein in more detail with reference to FIG. 3, the duplicate product module 106 may include computer-executable instructions operable to analyze prescription claim requests from a pharmacy computer 103 and/or electronic prescription orders from a prescriber computer 102 for determining whether the product indicated by the received request is the same or equivalent to a product which has previously been dispensed to the patient, and which may thus be a duplicate prescription for the same or similar product. The duplicate product module 106 may further include computer-executable instructions operable to, in response to identifying a duplicate prescription, notify the first prescriber of the product, the second prescriber of the product, the pharmacy, the patient, or any other entity or individual.

While performing any or all of the operations described herein, the duplicate product module 106 may access, or otherwise receive information from, the data storage device or database 142 and/or data files 134 to examine patient history, product fill history, other stored data and processing logic. The data storage device or database 142 and/or memory 128 may store, for example, but not be limited to, data containing the product fill history, equivalent product listings and attributes, prescriber contact information, pharmacy contact information, patient contact information, message templates, and corresponding default content, and the like.

It is appreciated that in example embodiments, the duplicate product module 106 may be provided in part or entirely within the service provider computer 104, or may be included as a separate computer device in operative communication with the service provider computer 104. In yet other embodiments, the duplicate product module 106 and/or the database 142 may be provided in part or entirely within one or more of the other entities' systems. If the service provider computer 104 includes the duplicate product module 106 and/or the database 142, then the database 142 could also be part of the memory 128, and the duplicate product module 106 can be stored in the memory 128.

The database 142 is represented as a single data storage device for simplicity. It is, however, appreciated that multiple physical and/or logical data storage devices or databases may be used to store the above mentioned data. For security and performance purposes, the service provider computer 104 may have a dedicated connection to the database 142. However, the service provider computer 104 may also communicate with the database 142 via the network 110 shown, or via another network. According to other embodiments, the service provider computer 104 may include the database 142 locally. The service provider computer 104 may also be part of a distributed or redundant DBMS.

The claims processor computer 108 may be similar to any of the prescriber computer 102, the pharmacy computer 103, or the service provider computer 104, and configured for receiving, processing, and fulfilling prescription claim requests, and, optionally, other transaction types, from the service provider computer 104 for claims adjudication or other transaction processing. In some embodiments, the claims processor computer 108 may represent an insurance payor system. Generally, the claims processor computer 108 may facilitate the determination of benefits, coverage, and/or extent of coverage for one or more prescription claim transactions. According to various embodiments, the claims processor computer 108 may be associated with, but is not limited to, a pharmaceutical benefits manager (PBM), an insurance company, a government payor-affiliated entity, another third-party payor, or a claims processor. According to another embodiment of the invention, the claims processor computer 108 may also be associated with providers of 100% copay plans such as discount programs. According to yet another embodiment, the claims processor computer 108 may be operated by, or otherwise included with, the service provider computer 104. It is further appreciated that, in some embodiments, such as one in which transaction processing is related to an electronic prescription order from a prescriber computer 102, the service provider computer 104 may not communicate with a claims processor computer 108, but instead may only communicate with the prescriber computer 102 and a pharmacy computer 103 (after which a prescription claim request may optionally be processed with a claims processor computer 108).

It is appreciated that each of the memories and data storage devices described herein for each of the prescriber computer 102, the pharmacy computer 103, and the service provider computer 104 can store data and information for subsequent retrieval. The memories and data storage devices can be in communication with each other and/or with other data storage devices, such as a centralized database, or other types of data storage devices. When needed, data or information stored in a memory or a data storage device may be transmitted to a centralized database capable of receiving data, information, or data records from more than one database or other data storage devices. In other embodiments, the data storage devices shown can be integrated or distributed into any number of databases or other data storage devices.

The network 110 may include any number of telecommunication and/or data networks, whether public, private, or a combination thereof, including a local area network, a wide area network, a publicly switched telephone network (PSTN), an intranet, the Internet, intermediate handheld data transfer devices, and/or any combination thereof, and may be wired and/or wireless. The network 110 may also allow for real-time, off-line, and/or batch transactions to be transmitted between the prescriber computer 102, the pharmacy computer 103, the service provider computer 104, and the claims processor computer 108. Due to network connectivity, various methodologies as described herein may be practiced in the context of distributed computing environments. Although the system 100 is shown for simplicity as including one intervening network 110, it is to be understood that any other network configuration is possible. For example, an intervening network 110 may include a plurality of networks, each with devices such as gateways and routers, for providing connectivity between or among networks 110. Instead of or in addition to a network 110, dedicated communication links may be used to connect the various devices in accordance with an example embodiment of the invention. For example, the service provider computer 104 may form the basis of the network 110 that interconnects the prescriber computer 102, the pharmacy computer 103, and the claims processor computer 108.

The system 100 shown in, and described with respect to, FIG. 1 is provided by way of example only. Numerous other operating environments, system architectures, and device configurations are possible. Accordingly, embodiments of the invention should not be construed as being limited to any particular operating environment, system architecture, or device configuration.

Operational Overview

Figure 2A:
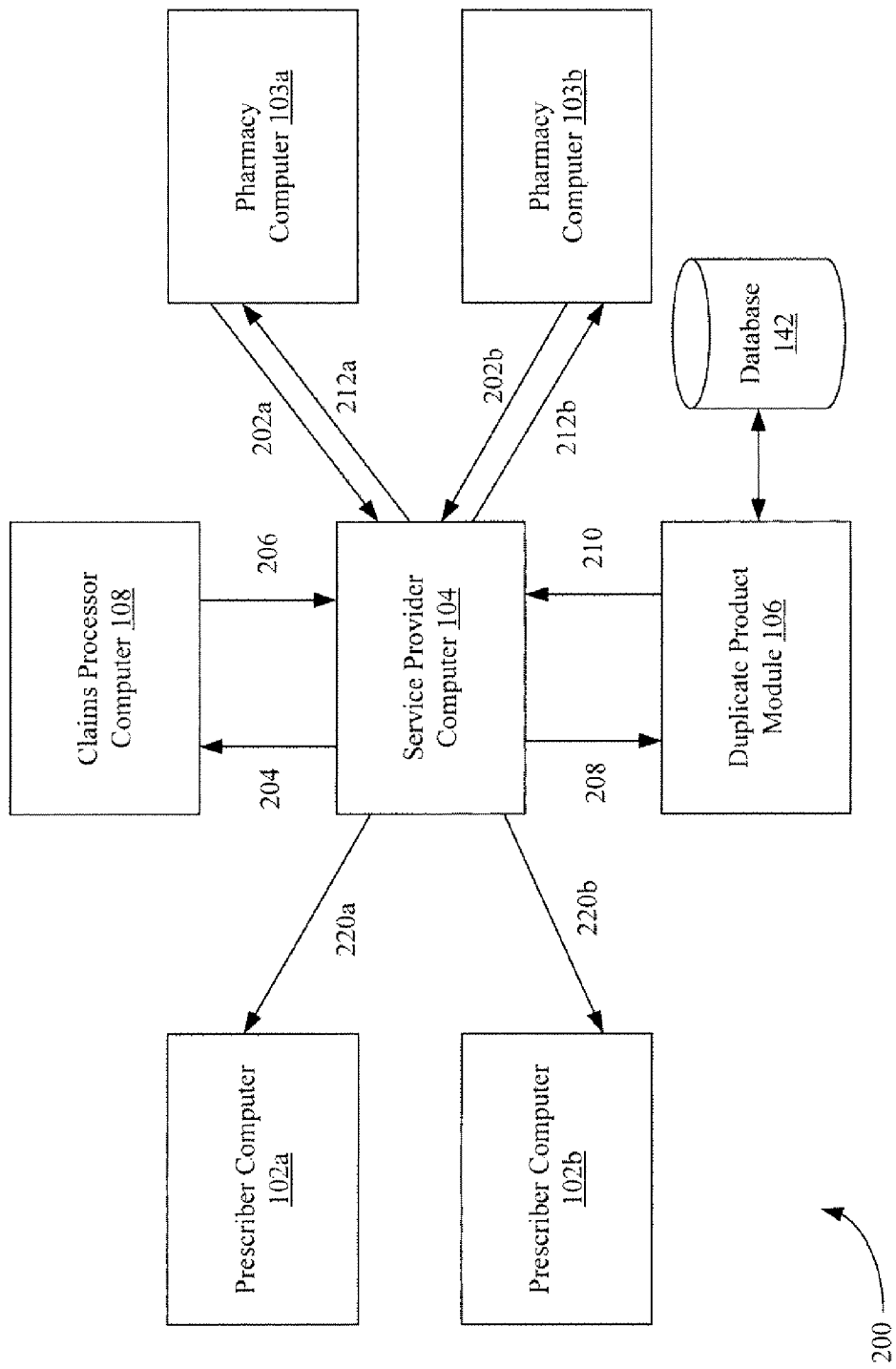
FIGS. 2A-2C illustrate example block diagrams for notifying of duplicate product prescriptions, according to example embodiments of the invention.
Figure 2B:
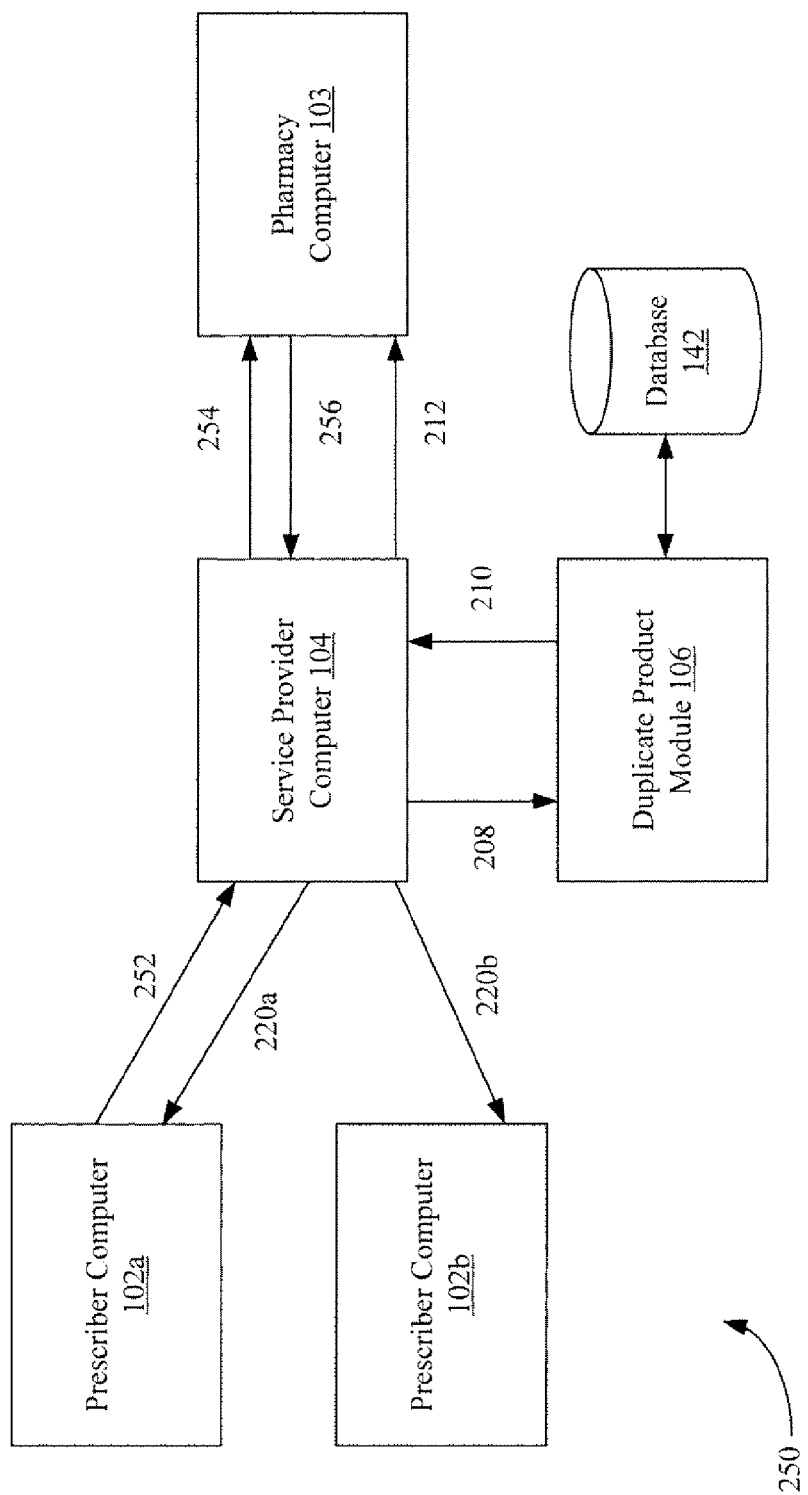
Figure 2C:
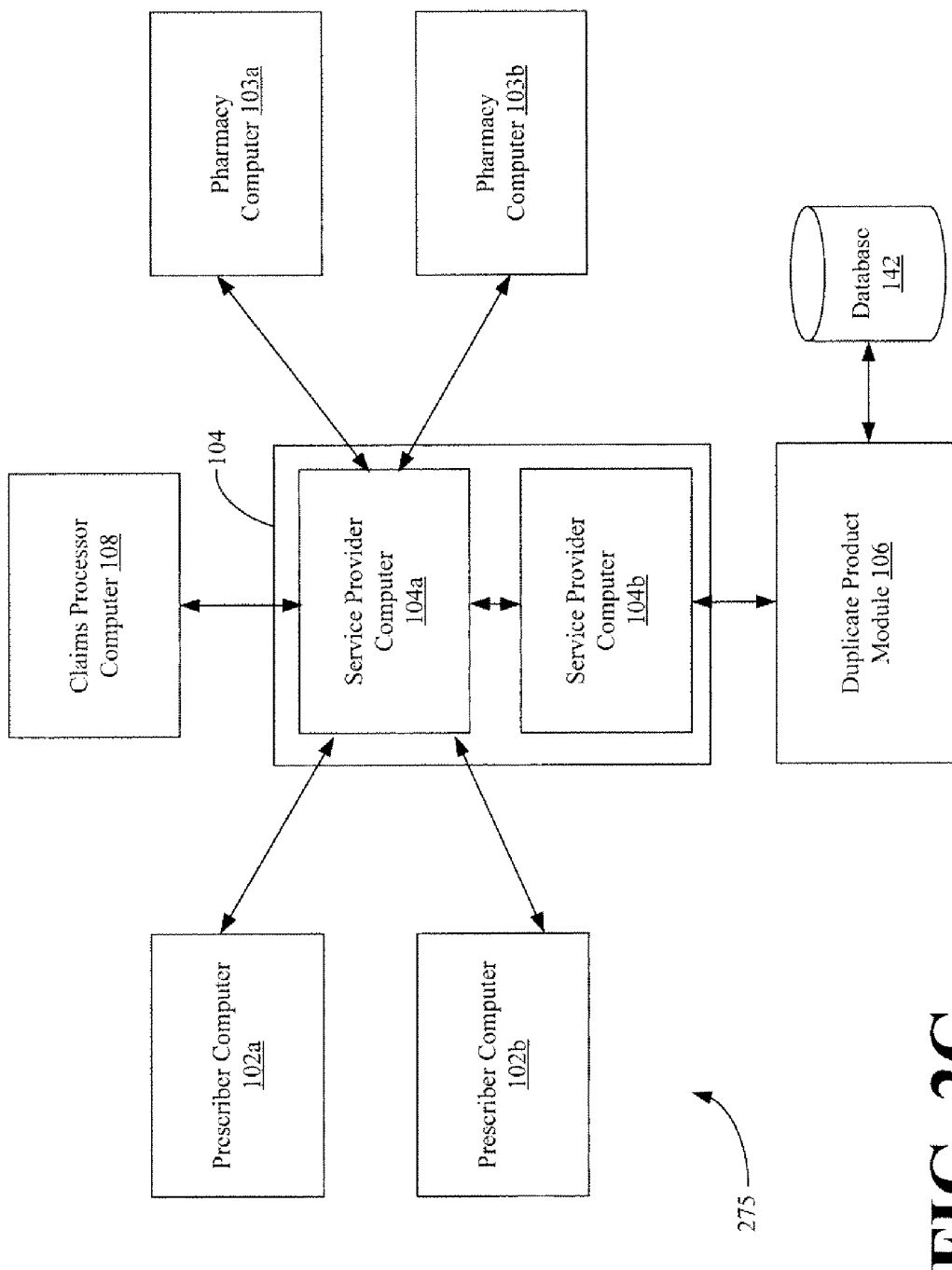

FIGS. 2A-2C illustrate block diagrams 200, 250, 275 representing example data flows for determining whether a prescription indicates a potentially duplicated prescription for the same or equivalent product, according to embodiments of the invention. FIG. 2A represents an example data flow 200 of performing the following operations upon receiving, at a service provider computer 104, prescription claim requests 202a, 202b from pharmacy computers 103a, 103b, and processing the prescription claim requests 202a, 202b with a claims processor computer 108. FIG. 2B represents an example data flow 250 of performing the following operations upon receiving, at a service provider computer 104, a prescription order 252 from a prescriber computer 102a, and processing the electronic prescription order 252 with a pharmacy computer 103. The data flows of, and the system relationships represented in, the block diagram of FIGS. 2A-2B will be discussed in conjunction with the flow diagram of FIG. 3.

FIG. 2C illustrates a variation of the block diagram of FIG. 2A. As shown by the data flow 275 of FIG. 2C, the service provider computer 104 may be comprised of two or more distinct service provider computers 104a and 104b that are in communication with each other. The service provider computer 104a may be operative with the prescriber computers 102a, 102b, the pharmacy computers 103a, 103b, and the claims processor computer 108, while the service provider computer 104b may be operative with other healthcare provider computers and/or other third-party entity computers. However, the service provider computer 104b may have a data processing arrangement with the service provider computer 104a. Under the data processing arrangement, the service provider computer 104a may be permitted to utilize or offer services of the service provider computer 104b, including the operations of the duplicate product module 106. Accordingly, the services accessible by the service provider computer 104b, including the services of the duplicate product module 106, may be available to the prescriber 102a, 102b, and/or the pharmacy computers 103a, 103b, via the service provider computers 104a and 104b. It is appreciated that the same or similar arrangement illustrated in FIG. 2C may be used to implement an architecture like that illustrated in FIG. 2B for processing electronic prescription orders from prescriber computers.

Figure 3:
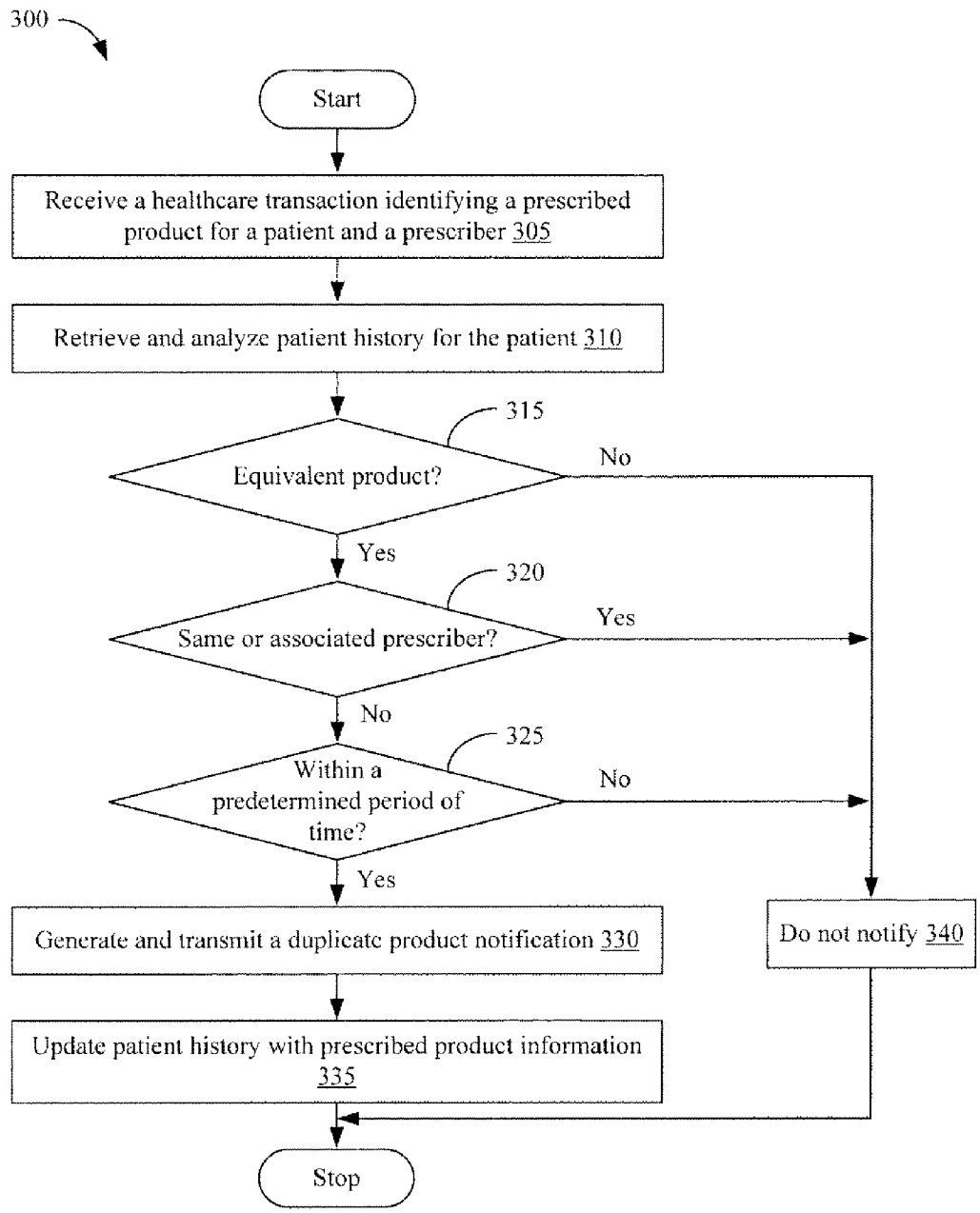
FIG. 3 illustrates an example flow diagram of a method for notifying of duplicate product prescriptions, according to an example embodiment of the invention.

Referring now to FIGS. 2A-2B and FIG. 3, an example method of determining whether a prescribed product is a duplicate prescribed product is described. The method 300 may begin at block 305 in which a service provider computer 104 receives a healthcare transaction that identifies at least a prescribed product, a patient, and a prescriber.

In one embodiment, as represented by the data flow 200 of FIG. 2A, the healthcare transaction can represent a "prescription claim request" 202 received from a pharmacy computer 103 for the purpose of processing a billing claim for adjudication with a claims processor computer 108. The prescription claim request 202 may include information relating to the patient, the prescriber, the payor, and the currently prescribed product (which can be interchangeably referred to as a "drug"). As an example, the prescription claim request 202 received by the service provider computer 104 may include, but need not be limited to, one or more of the following information, which may be in accordance with a version of National Council for Prescription Drug Programs (NCPDP) Telecommunication Standard, although other formats may be accepted by the service provider computer 104 as well:

Cardholder ID/Group Number associated with the patient,
a Banking Identification Number (BIN) and/or a Processor Control Number (PCN) associated with a designated claims processor,
an identification of the drug/product (e.g., National Drug Code (NDC)) provided to the patient,
a diagnosis/condition associated with the patient,
a prescriber identifier (e.g., National Provider Identifier (NPI) code, Drug Enforcement Administration (DEA) number, state-issued identification, etc.), and/or
a date of service.

In another embodiment, as represented by the data flow 250 of FIG. 2B, the healthcare transaction can represent an "electronic prescription order" 252 received from a prescriber computer 102 and for the purposes of ordering a new prescription for a patient (e.g., a NEWRX transaction with an e-prescribing system) or a refill prescription for a patient (e.g., a REFRES transaction with an e-prescribing system) via the service provider computer 104 to a pharmacy computer 103. The electronic prescription order 252 may be destined for a designated pharmacy computer 103 and may include a corresponding pharmacy identifier. The electronic prescription order 252 may also include information relating to the prescriber, the currently prescribed product, diagnosis/ailment/condition information, and/or the patient. For example, prescriber information may include a name and/or contact information (e.g., address and/or telephone number) and an identifier for the prescribing physician (e.g., a NPI code or DEA number). The currently prescribed product information may include a name of a prescribed product, a drug/product identifier (e.g., a NDC number), or other information such as quantity, refills, form (e.g., tablet, gel, etc.), dosage instructions, and/or date for the prescription. The diagnosis/ailment/condition information may include certain codes or identifiers to identify the condition(s) that the product is being prescribed to treat. The patient information may include a unique identifier, name, and/or contact information for the patient, as well as other patient information, such as a date of birth.

Accordingly, the following described operations may be performed on either of these two healthcare transactions. It is further appreciated that the above healthcare transaction descriptions are provided for illustrative purposes only, and that any other format and/or content may be included in transactions received at a service provider computer 104 that identify prescribed products.

Following block 305 is block 310, in which patient history is retrieved responsive to the healthcare transaction received at block 305. As described above, both a prescription claim request 202 and an electronic prescription order 252 include a patient identifier. The patient identifier may be, but is not limited to, social security, name, date of birth, health plan account identifier, any other unique identifier, or any combination thereof. Accordingly, at block 310 the service provider computer 104 and its duplicate product module 106 can retrieve patient history for the patient based at least in part on the patient identifying information received.

According to one embodiment, the patient history is representative of all or most healthcare transactions processed by the service provider computer 104 for the patient. For example, data from past prescription claim requests may be stored in a database 142 (or some other memory or data storage device). Similarly, data from past electronic prescription orders processed by the service provider computer 104 may also be stored. The patient history maintained by the service provider computer 104 thus represents a holistic view of a patient's prescribing history and can therefore aid in identifying prescription duplicates prescribed by different, unaffiliated prescribers and/or filled at different, unaffiliated pharmacies. The patient history is analyzed to determine whether the current prescribed product (indicated either by the prescription claim request 202 or the electronic prescription order 252) is a potential duplicate product to any of the products previously prescribed to the patient.

Duplicates may be determined based on any number of factors, including, but not limited to, any one or combination of the following: same drug, same or different dosage of the same drug, drugs of the same or equivalent chemistry, drugs of the same or similar therapy or therapeutic effects, same or similar conditions treated by the products, a branded version of the same product, a generic version of the same product, and the like. According to one embodiment, the duplicate product module 106 may include or otherwise access one or more tables (or other stored data) indicating known equivalent products. For example, a table may be provided as a look-up table against which a product identifier, name, or description can be compared to identify one or more known equivalent products based on any of the above factors (or any other factor). A product may have no equivalent products, one equivalent product, or more than one equivalent product. Accordingly, by performing a look-up against stored data of equivalent products, the duplicate product module 106 can retrieve one or more known equivalents of the current prescribed product, which are then compared to the patient's prescription history to determine whether the patient history reflects that one or more of these equivalent products have been previously prescribed or dispensed to the patient. It is appreciated, however, that other programming logic may be implemented with the duplicate product module 106 that does not require a look-up table, but instead may include any number of rules and factors considered to identify known equivalents of a current prescribed product.

At decision block 315, the duplicate product module 106 determines whether the patient history for the patient indicates that one or more known equivalent products have been previously prescribed or dispensed to the patient. If no known equivalent products are identified, then operations continue to block 340, where no notification is generated, and the method 300 may end. If, however, one or more equivalent products are identified at decision block 315, then operations continue to decision block 320.

At decision block 320, it is optionally determined whether the prescriber of the current prescribed product is the same prescriber or otherwise associated with the prescriber of the previous equivalent product or products identified. For example, according to one embodiment, the duplicate product module 106 may be programmed to only generate a notification (at block 330) if the prescribers are different. Otherwise, if the prescriber for the two products is the same, it may be assumed that the prescriber is aware of both prescriptions and would not desire to be notified. Different prescribers may be defined as different individuals and may optionally encompass prescribers that do not work together or are not associated or otherwise affiliated professionally such that they would not share or otherwise have access to the same patient history. However, in other embodiments, the duplicate product module 106 may be programmed to notify a prescriber of a potential duplicate product notwithstanding whether the same or affiliated prescriber prescribed the previous equivalent product. This may be the case if prescribers wish to be notified even of their own prior prescriptions for a patient. Similar processing may be performed to determine if the current pharmacy and previous pharmacy are the same, affiliated, or different. Depending upon the programming, if it is determined at decision block 320 that the previous prescriber is the same as or associated with the current prescriber, and if the duplicate product module 106 is configured to not notify the same or associated prescriber, then operations continue to block 340, where no notification is generated, and the method 300 may end. Otherwise, decision block 325 follows.

At decision block 325, details of each of the identified previous equivalent product prescriptions are analyzed to determine whether the current prescription is actually a duplicate, or whether it may simply be a refill for the previous prescription. Accordingly, the duplicate product module 106 is operable to analyze the temporal context between the previous prescription for the equivalent product and the current product prescription. For example, one factor that may indicate a duplicate product prescription is if the administration periods for each product overlap. Overlapping periods may be approximated by analyzing the dispense date (or request date) of the previous equivalent product prescription and the dose and quantity, to determine whether the previous product would still be taken by the patient at the same time the current product would be taken. In other embodiments, however, administration periods may not overlap, but still encourage a notification, such as if the current product would be taken within a predetermined period of time from the previous equivalent product to raise concern (e.g., safety risks, criminal, habitual, or addictive behaviors, etc.). In one example, if the previous equivalent and current products are of the type for which administration should not be repeated within a predetermined period of time, the duplicate product module 106 may be configured to identify this predetermined period of time based on the products or product type and generate a notification, accordingly. In another example, if the previous equivalent product was prescribed to treat a first condition, and the current product is prescribed to treat a second condition, a notification may be beneficial if the second prescriber of the current product was unaware of the recent administration of the previous equivalent product. In another example, the timing of the previous equivalent product prescription may be compared to the current product prescription to determine whether the current product prescription is a refill of the earlier product (which may also be indicated by the prescriber indicated) or a new prescription for the same treatment (e.g., after refills ran out). The duplicate product module 106 may be configured not to generate a subsequent notification if it can be determined that the current product prescription is simply the next filled prescription for the same treatment (e.g., refill or new fill). It is appreciated that any number of other factors may be analyzed by the duplicate product module 106 to determine whether within a period of time, such as, that the administration periods would be overlapping or that the use is inadvisable or suspicious. For example, in one embodiment, if a patient is being dispensed two different strengths of the same product on the same day at the same pharmacy, then it may be concluded that both product doses are needed to fulfill the prescribed dosage (e.g., drug A in 10 mg and drug A in 2 mg to fill a 12 mg prescription, etc.). As such, it may be concluded that no duplicate product notification is to be transmitted. However, in another example, if a patient is being prescribed a same or different strength of a controlled substance at two different pharmacies, the it may be concluded that a duplicate product notification should be transmitted.

If it is determined at decision block 325 that the previous equivalent product was prescribed and/or dispensed at a time sufficiently earlier than, and/or spaced apart from, the current product, or if the timing indicates a refill or new fill for the same treatment, then block 340 may follow, where no notification is generated and the method 300 may end. Otherwise, block 330 follows.

At block 330, the duplicate product module 106 is configured to generate and transmit a duplicate product notification to one or more individuals and/or entities associated with a previous equivalent product prescription, the current prescribed product prescription, or both. For example, one or more duplicate product notifications 220a, 220b may be transmitted to the current prescriber computer 102a and/or the previous prescriber computer 102b, as illustrated in FIGS. 2A-2B. Similarly, one or more duplicate product notifications 212a, 212b may be transmitted to the pharmacy computers 103a, 103b where the current prescription and/or the previous prescription was filled for the patient, as illustrated in FIGS. 2A-2B. It is further appreciated that product notifications may also, or instead, be transmitted to the patient, to a monitoring authority (e.g., controlled substance monitoring authority, law enforcement, etc.), a reporting entity, an auditor, and the like.

According to various embodiments, a duplicate product notification may include, but is not limited to, an identity of the patient, an identity of the previous equivalent product, a date associated with the previous equivalent product, an identity of the current prescribed product, a date associated with the current prescribed product, an identity of the pharmacy where the previous equivalent product was filled, an identity of the pharmacy where the current prescribed product is being filled, or any combinations thereof. In some embodiments, the identity of the previous prescriber, the current prescriber, or both may also be indicated in the duplicate product notification; although, in other embodiments, prescriber identities may be withheld. Similarly, for some duplicate product notifications, such as those going to reporting entities or auditors, the prescribers' and/or the patient identities may not be included to retain anonymity. It is appreciated that any other information may be included in a duplicate product notification, and that the aforementioned information is provided for illustrative purposes.

Duplicate product notifications may be embodied in a variety of forms, including, but not limited to, an email, a facsimile, a SMS text message, a network-based message (e.g., over a healthcare transaction network, etc.), an Internet-based message (e.g., via a web-based interface), a mailed correspondence, a telephonic notification (e.g., manual voice call or message, an interactive voice response unit (IVR) placed message, etc.), and the like. For example, when transmitting a duplicate product notification 220a, 220b to a prescriber or a patient, an email, facsimile, or text message may be transmitted; though, when transmitting a duplicate product notification 212a, 212b to a pharmacy computer 103, then network-based messaging from the service provider computer 104 may be used. Similarly, duplicate product notifications to other third-party systems, such as monitoring authorities, auditors, reporting entities, and the like, may best be transmitted via email, Internet-based communications (e.g., if the entity has a web-based interface), or mailed correspondence.

Following block 330 is block 335, in which the patient history is updated to reflect the current prescribed product information. In one embodiment, the patient history may be updated to indicate whether one or more duplicate product notifications were sent, and if so, to whom.

The method 300 may end after blocks 335 or 340, having determined whether a current prescribed product is potentially a duplicate to a previously prescribed equivalent product and transmitting one or more notifications regarding the occurrence of the same.

Example scenarios in which the operations of the method 300 of FIG. 3 are performed are now described with reference to FIGS. 2A-2B. FIG. 2A illustrates a first example scenario for processing a prescription claim request 202 received from a pharmacy, where there are two prescriber computers 102a, 102b, two pharmacy computers 103a, 103b, and a claims processor computer 108, each in communication with a service provider computer 104. In this example, the first prescriber computer 102a is associated with the prescriber of a current prescribed product, while the second prescriber computer 102b is associated with the prescriber of a previously prescribed equivalent product. Similarly, the first pharmacy computer 103a is associated with the pharmacy at which the current prescribed product is being filled and from which the current prescription claim request 202a is transmitted to the service provider computer 104, while the second pharmacy computer 103b is associated with the pharmacy at which the previously prescribed equivalent product was filled, which may have also been associated with a previous prescription claim request 202b.

Accordingly, upon receiving the current prescription claim request 202a from the first pharmacy computer 103a, the service provider computer 104 performs the duplicate product processing by sending an inquiry 208 to, and receiving a response 210 from, the duplicate product module 106. In one embodiment, duplicate product processing is performed after adjudication of the claim request 202a with the claims processor computer 108, which may be performed via a claim request 204 for adjudication and response 206 indicating the adjudicated results of the request. In this embodiment, duplicate processing may only be performed if the claim is not rejected, so as to minimize unnecessary processing. However, in other embodiments, the service provider computer 104 may perform duplicate product processing before or concurrent with adjudication processing performed by the claims processor computer 108.

If the operations performed by the duplicate product module 106 determine that an equivalent product has been previously prescribed and dispensed to the patient, and that a notification should be sent, as described with reference to FIG. 3, then one or more duplicate product notifications can be sent. As illustrated in FIG. 2A, duplicate product notifications 220b, 220a can be sent to the second prescriber computer 102b (or directly to the prescriber, such as via email or text) that prescribed the previous equivalent product, and/or to the first prescriber computer 102a (or to the prescriber directly) that prescribed the current product, respectively. Similarly, duplicate product notifications 212a, 212b may also be sent to the first pharmacy computer 103a that initiated the prescription claim request 202a for the current prescribed product, and/or to the second pharmacy computer 103b, which dispensed the previous equivalent product to the patient. Also as described above with reference to FIG. 3, any number of other parties may be notified in addition to, or instead of, the prescribers and/or pharmacies involved.

With reference to FIG. 2B, in a second example scenario for processing an electronic prescription order, there are two prescriber computers 102a, 102b and at least one pharmacy computer 103, each in communication with a service provider computer 104. The first prescriber computer 102a is associated with the prescriber of a current prescribed product and from which the electronic prescription order 252 is transmitted to the service provider computer 104, while the second prescriber computer 102b is associated with the prescriber of a previously prescribed equivalent product. Similarly, the pharmacy computer 103 is associated with the pharmacy where the electronic prescription claim request will be routed and at which the current prescribed product is to be filled. Although a second pharmacy computer is not illustrated, a subsequent notification may be transmitted thereto, in other embodiments, as described above.

Accordingly, an electronic prescription order 252 from the first prescriber computer 102a is received by the service provider computer 104 for electronically requesting 254 a prescription at the pharmacy computer 103a on behalf of the patient. As part of this processing, the service provider computer 104 can initiate an inquiry 208 to, and receive a response 210 from, the duplicate product module 106 to determine whether the electronic prescription order 252 identifies a duplicate product that encourages subsequent notification. This duplicate product processing may be performed prior to, concurrent with, or after submitting the electronic prescription request 254 to the pharmacy computer 103 and receiving the response 256 thereto. In the event that the service provider computer 104 and its duplicate product module 106 determine that there may potentially have been previous equivalent products prescribed to the patient, as described in more detail with reference to FIG. 3, the service provider computer may transmit one or more duplicate product notifications 220a, 220b, 212 to the first or second prescriber and/or the pharmacy.

In response to receiving a duplicate product notification, a prescriber may follow-up with the patient, prescribe a different product, update patient records accordingly, follow-up with the other prescriber, and/or notify the appropriate authorities. A pharmacy receiving a duplicate notification may likewise follow-up with the patient, recommend alternative therapies, update patient records, and/or notify the appropriate authorities. In some instances, if a prescriber or pharmacy is notified prior to the product being dispensed to the patient, the prescriber or pharmacy may intervene to prevent dispensing the product to the patient. Preventing product from being dispensed may be particularly useful if the duplicate product may be harmful or indicative of illicit behavior by the patient.

Accordingly, the example systems and methods described herein provide the ability to analyze healthcare transactions, which include prescription claim transactions and electronic prescription orders, to determine whether the current prescribed product identified by the transaction may potentially be a duplicate or equivalent product to a previously prescribed product. A service provider, which is transactionally situated "between" prescribers, pharmacies, and claims processors, is uniquely positioned to gather a more complete patient history than any of these systems alone. The service provider can therefore make more informed and intelligent determinations of the prescribing activities of patients due to this more complete view of the patients' histories.

Embodiments of the invention are described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

It will be appreciated that each of the memories and data storage devices described herein can store data and information for subsequent retrieval. The memories and databases can be in communication with each other and/or other databases, such as a centralized database, or other types of data storage devices. When needed, data or information stored in a memory or database may be transmitted to a centralized database capable of receiving data, information, or data records from more than one database or other data storage devices. In other embodiments, the databases shown can be integrated or distributed into any number of databases or other data storage devices.

It will also be appreciated that each of the I/O interfaces described herein may facilitate communication between a processor and various I/O devices, such as a keyboard, mouse, printer, microphone, speaker, monitor, bar code readers/scanners, RFID readers, and the like. Likewise, each of the network interfaces described herein may take any of a number of forms, such as a network interface card, a modem, a wireless network card, and the like.

It will further be appreciated that while certain computers have been illustrated herein as a single computer or processor, the illustrated computers may actually be comprised of a group of computers or processors, according to an example embodiment of the invention.

Many modifications and other embodiments of the invention will come to mind to one skilled in the art to which this invention pertains and having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for processing prescriptions, comprising:
   receiving, by a service provider computer, a healthcare transaction that identifies a current prescribed product, a patient, and a current prescriber who prescribed the current prescribed product;
   retrieving, by the service provider computer, patient history for the patient;
   determining, by the service provider computer, based at least in part on the patient history:
      that the patient has previously received a previous equivalent product that is equivalent to the current prescribed product identified in the healthcare transaction, and
      an identity of a previous prescriber of the previous equivalent product;
   determining that the previous prescriber is different from the current prescriber and that the previous prescriber and the current prescriber are not professionally associated;
   transmitting a notification to at least one of: (a) the previous prescriber; (b) the current prescriber; (c) a pharmacy; or (d) the patient, wherein the notification identifies potential duplicate products; and
   prior to transmitting the notification, analyzing the patient history for the patient to identify that the previous equivalent product was dispensed to the patient less than a predetermined period of time prior to a date associated with the healthcare transaction request.

2. The method of claim 1, wherein the notification is transmitted to the previous prescriber.

3. The method of claim 1, wherein determining that the patient has previously received the previous equivalent product comprises comparing the current prescribed product to stored data indicating a plurality of equivalent products, wherein equivalent products are determined based at least in part on at least one of: (a) one or more active ingredients of the respective products; (b) therapeutic effects provided by the respective products; (c) conditions treated by the respective products, (d) dosage; (e) strength; or (f) chemical equivalency of the respective products.

4. The method of claim 1, wherein the notification is a first notification, and further comprising transmitting a second notification to at least one of: (a) the other of the previous prescriber or the current prescriber; (b) a monitoring authority; (c) a pharmacy computer; (d) the patient; or (e) law enforcement.

5. The method of claim 1, wherein the notification is transmitted via one of: (a) an email; (b) a facsimile; (c) a text message; (d) a network-based message; (e) an Internet-based message; (f) mailed correspondence; or (g) a telephonic notification.

6. The method of claim 1, wherein the healthcare transaction is received from a first pharmacy computer for dispensing the current prescribed product at a first pharmacy, and wherein the previous equivalent product was dispensed to the patient at a second pharmacy not associated with the first pharmacy.

7. The method of claim 1, wherein the healthcare transaction is received from a first pharmacy computer for dispensing the current prescribed product at a first pharmacy, and wherein the previous equivalent product was dispensed to the patient at the first pharmacy.

8. The method of claim 1, wherein the notification comprises an identity of the patient, an identity of the previous equivalent product, a date associated with the previous equivalent product, an identity of the current prescribed product, and a date associated with the current prescribed product.

9. The method of claim 1, wherein the healthcare transaction comprises one of: (a) an electronic prescription order received from a prescriber computer; or (b) a prescription claim request received from a pharmacy computer.

10. The method of claim 1, wherein the patient history is maintained by the service provider computer.

11. The method of claim 1, further comprising updating the patient history for the patient with information associated with the current prescribed product.

12. A system, comprising:
 at least one memory for storing computer-executable instructions; and
 at least one processor configured to access the memory and further configured to execute the computer-executable instructions to:
  receive a healthcare transaction that identifies a current prescribed product, a patient, and a current prescriber who prescribed the current prescribed product;
  retrieve patient history for the patient;
  determine, based at least in part on the patient history, that the patient has previously received a previous equivalent product equivalent to the current prescribed product identified in the healthcare transaction and an identity of a previous prescriber for the previous equivalent product;
  determine that the previous prescriber is different from the current prescriber and that the previous prescriber and the current prescriber are not professionally associated; and
  transmit a notification to at least one of: (a) the previous prescriber; (b) the current prescriber; (c) a pharmacy; or (d) the patient, wherein the notification identifies potential duplicate products,
 wherein, prior to transmitting the notification, the at least one processor is further configured to execute the computer-executable instructions to analyze the patient history for the patient to identify that the previous equivalent product was dispensed to the patient less than a predetermined period of time prior to a date associated with the healthcare transaction request.

13. The system of claim 12, wherein the notification is transmitted to the previous prescriber.

14. The system of claim 12, wherein the memory further comprises stored data indicating a plurality of equivalent products, wherein equivalent products are determined based at least in part on at least one of: (a) one or more active ingredients of the respective products; (b) therapeutic effects provided by the respective products; (c) conditions treated by the respective products, (d) dosage; (e) strength; or (f) chemical equivalency of the respective products.

15. The system of claim 12, wherein the notification is transmitted via one of: (a) an email; (b) a facsimile; (c) a text message; (d) a network-based message; (e) an Internet-based message; (f) mailed correspondence; or (g) a telephonic notification.

16. The system of claim 12, wherein the healthcare transaction is received from a first pharmacy computer for dispensing the current prescribed product at a first pharmacy, and wherein the previous equivalent product was dispensed to the patient at one of: (a) a second pharmacy not associated with the first pharmacy; or (b) the first pharmacy.

17. The system of claim 12, wherein the healthcare transaction comprises one of: (a) an electronic prescription order received from a prescriber computer; or (b) a prescription claim request received from a pharmacy computer.

18. The system of claim 12, wherein the at least one processor is further configured to execute the computer-executable instructions to update the patient history for the patient with information associated with the current prescribed product.

* * * * *